(12) United States Patent
Belokin

(10) Patent No.: US 6,390,311 B1
(45) Date of Patent: May 21, 2002

(54) AMBULATORY DISPENSER RACK

(75) Inventor: Paul Belokin, Denton County, TX (US)

(73) Assignee: Martin Paul, Inc., Denton, TX (US)

( * ) Notice: Subject to any disclaimer, the term of this patent is extended or adjusted under 35 U.S.C. 154(b) by 0 days.

(21) Appl. No.: 09/629,132

(22) Filed: Jul. 31, 2000

(51) Int. Cl.[7] ................................................ A47F 5/00
(52) U.S. Cl. ...................... 211/204; 211/206; 211/189; 248/129; 280/79.3
(58) Field of Search ..................... 280/79.3; 211/206, 211/204, 85.18, 71.01, 207, 189, 193, 123, 113, 117; 248/125, 129

(56) References Cited

U.S. PATENT DOCUMENTS

| | | | | |
|---|---|---|---|---|
| 2,947,422 A | * | 8/1960 | Sudbery | |
| 3,146,892 A | * | 9/1964 | White | |
| 4,832,294 A | * | 5/1989 | Eidem | 248/125 |
| 4,934,015 A | * | 6/1990 | Mink | 211/206 X |
| 4,945,592 A | * | 8/1990 | Sims et al. | 248/129 |
| 5,022,538 A | * | 6/1991 | Richmond et al. | 211/113 |
| 5,535,898 A | * | 7/1996 | Burgess et al. | 211/206 |
| 5,556,065 A | * | 9/1996 | Wadley | 248/129 |
| 5,617,962 A | * | 4/1997 | Chen | 211/206 |
| 5,660,637 A | * | 8/1997 | Dodge | 280/79.3 X |
| 5,718,344 A | * | 2/1998 | Joldeson et al. | 211/206 |
| 6,224,072 B1 | * | 5/2001 | Weck et al. | 211/204 X |

* cited by examiner

Primary Examiner—Robert W. Gibson, Jr.
(74) Attorney, Agent, or Firm—Jack A. Kanz

(57) ABSTRACT

A rack for supporting fluid dispensers for use in a sterile environment is formed by two substantially parallel vertical beams supported on a base. The base comprises a cross member attached between two foot members which ride on quadruplicate wheels. A horizontal bar connects the vertically extending beams and a support bar supported at the top of at least one of the vertical beams carries hooks for supporting IV bags and the like. The rack is sufficiently steady and stable to be used for support and transport of IV bags and the like for an ambulatory patient. The rack is also readily disassembled and cleaned so that it may be repeatedly used in sterile environments such as surgical operating rooms and the like.

20 Claims, 5 Drawing Sheets

AMBULATORY DISPENSER RACK

This invention relates to apparatus for organizing and supporting a plurality of fluid dispensers such as IV bags and the like. More particularly, it relates to dispenser racks, stands or the like adapted for ambulatory movement while supporting and organizing a plurality of liquid and/or gas dispensers and/or collectors which may be readily disassembled, cleaned and re-assembled for use in sterile environments such as hospital surgical areas and the like.

Various pole stands and the like are currently used in hospital environments to act as overhead supports for fluid dispensing apparatus such as intravenous (IV) bags and the like. Conventionally, such stands comprise a single vertical post with laterally extending beams or arms from which the fluid dispensers are suspended. Unitary post stands with laterally extending arms are inherently unstable and are frequently overturned by overweighting with dispensers or by entanglement of drip tubes with patients or attending staff. Even though such stands may function reasonably well in a stationary bedside position, they are extremely unstable and unacceptable for use in assisting an unsteady ambulatory patient in walking while attached to drip tubes from IV bags or fluid drainage bags supported by the stand.

Similar (or the same) pole stands are often used in surgical operating rooms to support IV bags, fluid collection bags and the like used by the attending anesthesiologist, surgeon or nursing staff Single post stands are not only unstable as discussed above but, when used in the operating room, often support a plurality of fluid dispensers such as IV bags and the like, all suspended from a single post. Organization of the IV bags and attending drip tubes for easy observation and management becomes increasingly difficult as the number of drip tubes increases. Likewise, the possibility of entanglement of drip tubes with other operating room equipment and staff increases dramatically with increased number of tubes, and organization of the tubes for convenient observation and management becomes extremely difficult. Furthermore, all equipment used in surgical operating rooms must be easily cleaned and sterilized or discarded.

The present invention provides an extremely stable dispenser and/or collector rack which is easily disassembled and reassembled for cleaning and reuse. The rack comprises a pair of vertical beam. s mounted on an H-shaped quadruplicate-wheeled base support. A support bar mounted near the upper ends of the vertical beams carries hooks for overhead mounting of IV bags and the like. Because of the H-shaped base support and use of parallel vertical beams, the rack is mobile yet extremely stable and permits organization of IV bags and the like for easy and convenient observation and management. Because of the inherent stability of the structure, it may also be used as a walker for providing stability to an ambulatory patient while carrying fluid-dispensing and/or fluid collection apparatus attached to the patient. The entire structure is designed to permit rapid, simple and easy disassembly for cleaning and reassembly for reuse completely by hand without using any tools. Each component is also designed to permit sterilization by conventional means or replacement after use so that the structure meets all sterility requirements for operating room use. Other features and advantage of the invention will become more readily understood from the following detailed description taken in connection with the appended claims and attached drawing in which:

Figure 1:
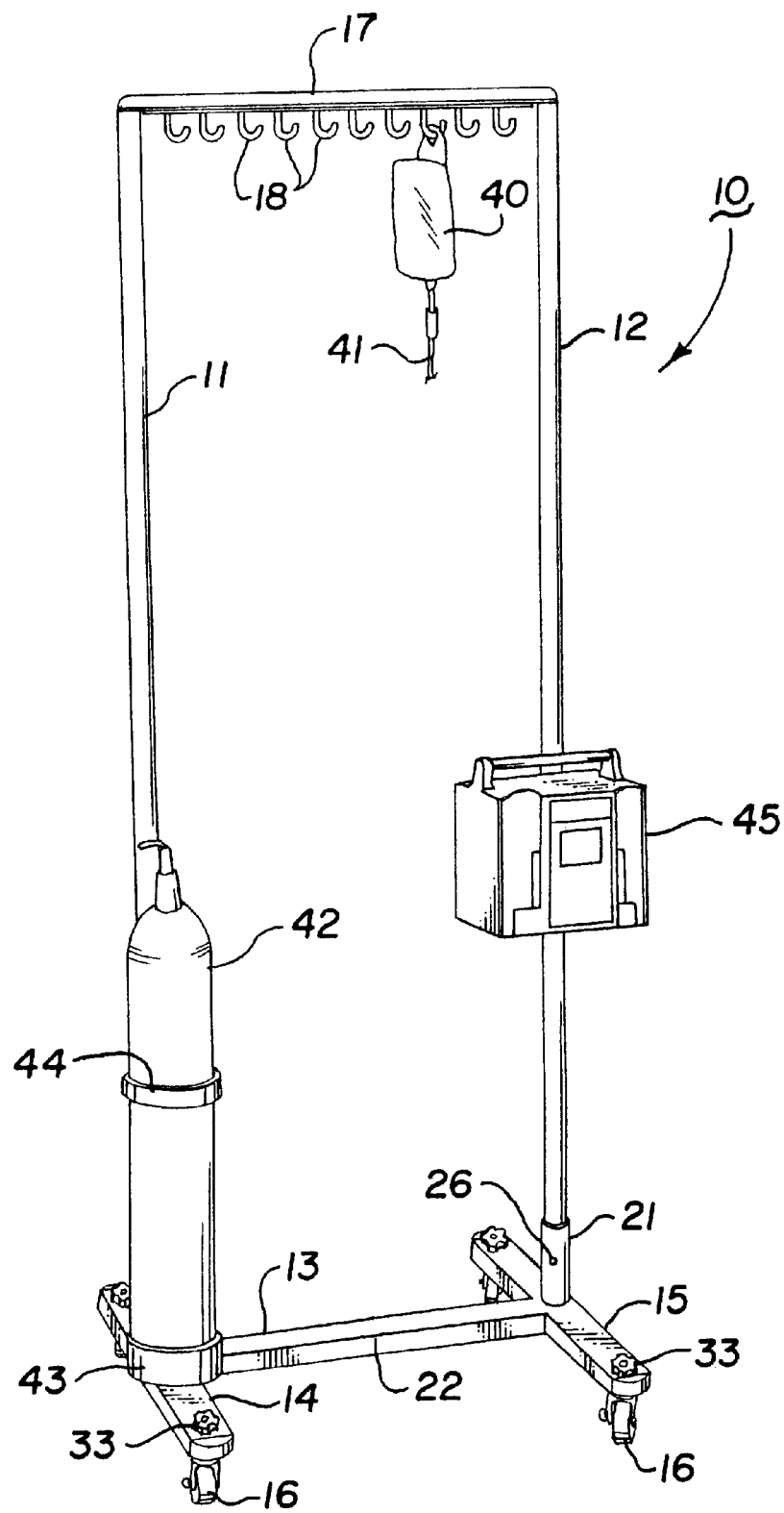
FIG. 1 is a front perspective view of one embodiment of a mobile rack made in accordance with the invention.

Throughout the several views of the drawing like numerals are used to indicate like parts. The drawing figures are not to scale. They are intended to disclose the inventive concepts by illustration and are incorporated herein to illustrate presently preferred embodiments of the invention. The drawing should not be construed as limiting the invention to the illustrated and described embodiments.

In FIG. 1 the invention is illustrated as a wheeled rack 10 comprising substantially parallel vertically extending beams 11, 12 supported on an H-shaped base support comprising a horizontal cross member 13 connected between two foot members 14, 15. Foot members 14, 15 each comprise a central body joined with the cross member 13 at opposite ends thereof and have ends extending in opposite directions from and normal to the horizontal axis of the cross member 13. A wheel 16 or caster is attached to each end of each of the foot members 14, 15. For ease of manipulation, the wheels 16 are preferably swivelably mounted on vertical studs.

Figure 2:
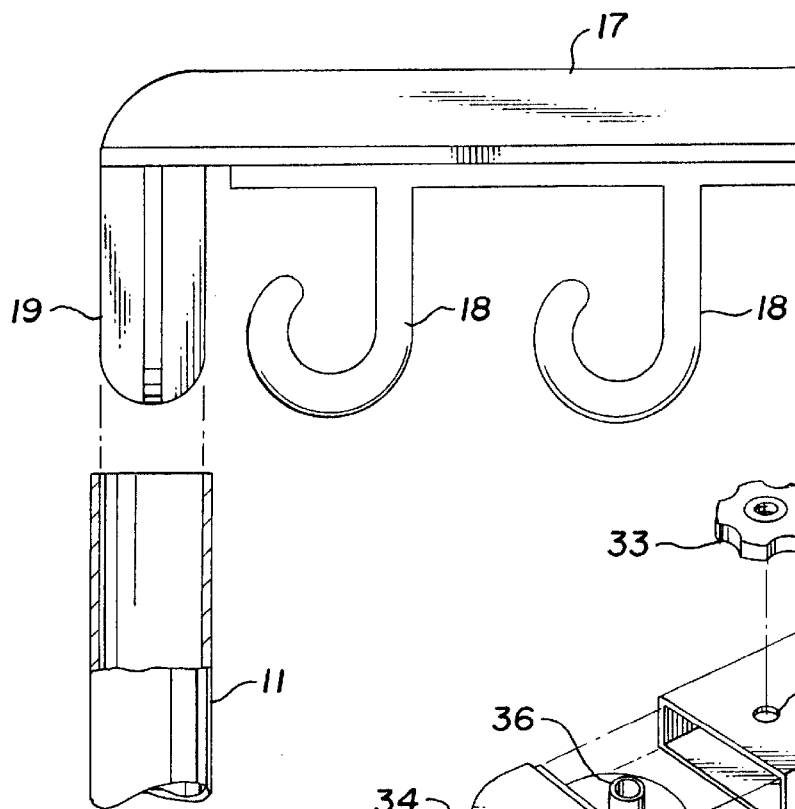
FIG. 2 is a fragmentary view, partially in section, of the assembly of a support bar connecting the vertical beams in the mobile dispenser rack of FIG. 1.

A pair of parallel beams 11, 12 is mounted on the support base to extend vertically substantially parallel with each other. In the embodiment illustrated in FIGS. 1 and 2 at least the upper ends of beams 11, 12 are hollow and are secured together by a connecting support bar 17 which carries a plurality of outwardly or downwardly projecting hooks 18. A downwardly depending plug 19 depends from each end of the connecting support bar 17 (see FIG. 2). The plugs 19 are adapted to fit within the hollow ends of the vertically extending members 11, 12 as shown in FIG. 2. Of course, the connection may be reversed by forming recesses in the ends of support bar 17 and inserting the ends of the beams 11, 12 in the recesses.

Since one primary use of the dispenser rack of the invention requires sterile environments, the rack 10 is designed to be readily and easily disassembled, cleaned and reassembled. Preferably, disassembly and reassembly should be accomplished without the use of any tools. Accordingly, the vertical parallel beams 11, 12 are secured to the base support by simple tongue and socket arrangements. In the embodiments illustrated, sockets 20, 21 extend vertically from the base support, preferably intermediate the ends of foot members 14, 16. Sockets 20, 21 are sized to receive the lower ends of vertically extending beams 11, 12. In the preferred embodiment, the beams 11, 12 fit snugly within sockets 20, 21. It will be readily appreciated, however, that if the lower ends of beams 11, 12 are hollow, sockets 20, 21 may be replaced by upwardly extending studs which fit inside the hollow ends of vertically extending beams 11, 12. The sockets 20, 21 (or studs) are axially elongated to form axially extended socket and tongue connections which rigidly secure the beams 11, 12 to the base support.

To avoid use of fixed attachments and tools for assembly, disassembly and reassembly, the entire rack assembly may be secured together by tension. As illustrated in FIG. 1, a groove 22 is formed in the underside of cross member 13 and the ends of the cross member 13 bent slightly downwardly from the center portion by forcing the edges of the groove toward each other. When the cross member 13 is so bent, the central axes of the sockets 20, 21 are splayed slightly outwardly from the vertical as indicated by the arrows in FIG. 3. Accordingly, when vertically extending beams 11, 12 are inserted therein, the upper ends of vertical beams 11, 12 are also splayed outwardly. However, the plugs 19 on the ends connecting bar 17 are spaced apart a distance equal to the distance separating sockets 20, 21. Accordingly, when plugs 19 are inserted into the top ends of the beams 11, 12, the ends must be drawn toward each other. When the plugs 19 are inserted within the ends of the beams, the ends of the vertical beams tend to return to the outwardly splayed position, thus placing connecting support bar 17 under tension. In this condition, lateral forces are applied to the internal surfaces of the upper ends of beams 11, 12 by plugs 19 and to the outer surfaces of the lower ends of beams 11, 12 by sockets 20, 21. Thus the entire assembly is held together by the friction caused by such tension.

Other methods may be used to place the beam end connections under tension. For example, the sockets 20, 21 (or studs) could be mounted slightly splayed (inwardly or outwardly) with respect to the horizontal surface of the base support or the distance separating the sockets 20, 21 (or studs) could be more or less than the distance separating the plugs 19. Any of these arrangements or combinations of these arrangements (or other suitable arrangements) may be used to maintain the connecting joints under sufficient tension to maintain integrity of the assembly without using bolts, screws or the like.

Figure 5:
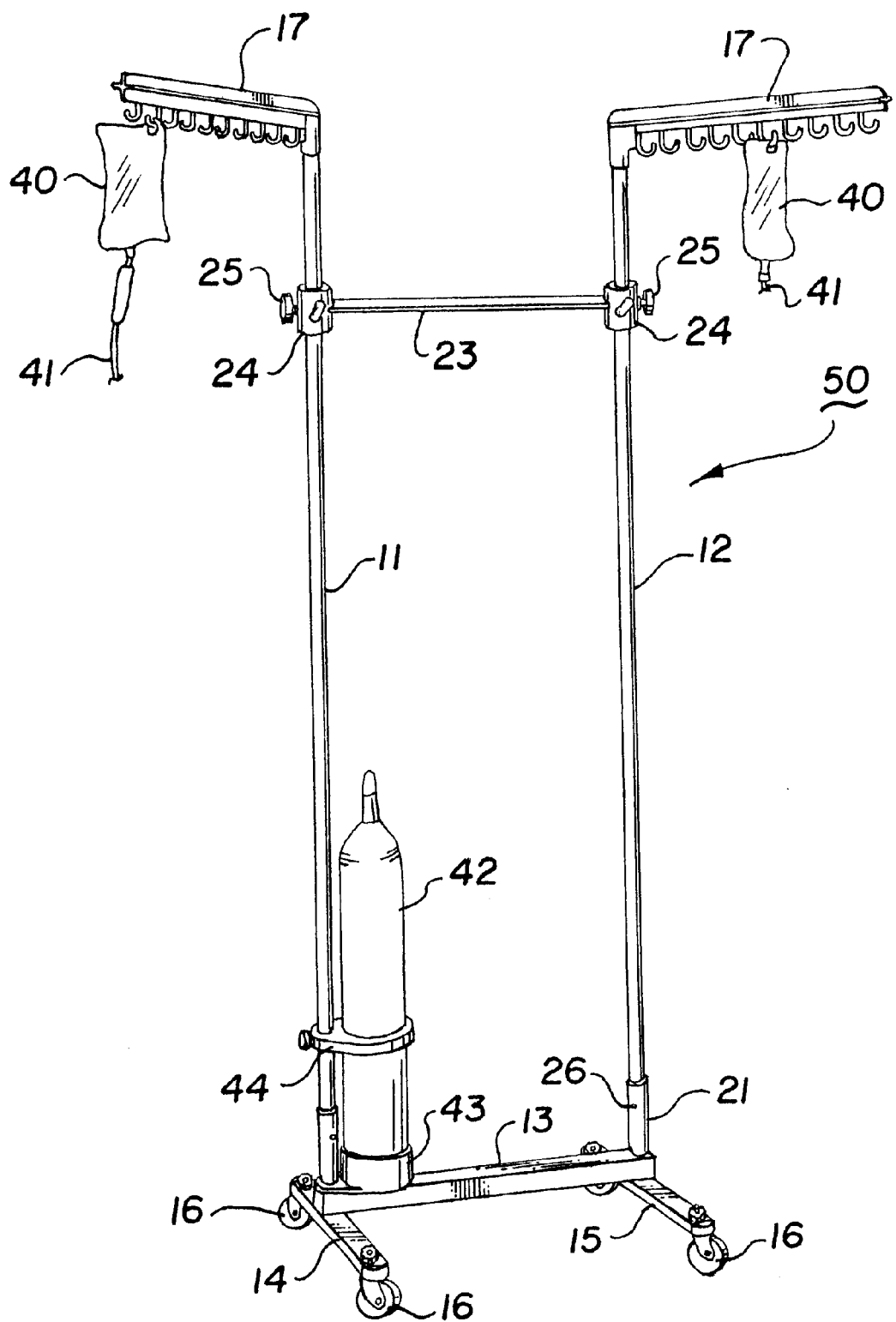
FIG. 5 is a front perspective view of an alternative embodiment of the rack of the invention.
Figure 11:
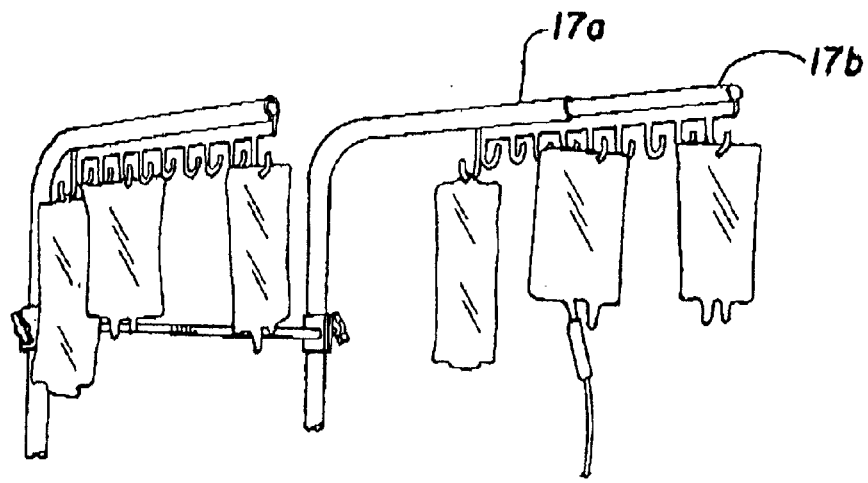
FIG. 11 is a front perspective view of a variable length bar supported by one of the vertical beams of a dispenser rack in accordance with the invention.

An alternative configuration 50 is shown in FIG. 5 where a moveable crossbar 23 is mounted between the vertical beams 11, 12. Moveable crossbar 23 carries a channel or sleeve 24 on each end which is slideable along the length of beams 11, 12. Each sleeve 24 carries at least one attachment screw 25 mounted in a threaded aperture in the sleeve 24. Crossbar 23 thus serves the function of a connecting bar which holds the vertical beams in fixed relationship.

Where a moveable crossbar 23 is used as the connecting bar (as in FIG. 5), the support bar 17 may be separated into two (2) support bars, each independently mounted on the end of one of the vertical beams 11, 12. However, in this embodiment the support bar (or bars) 17 is not used to interconnect the vertical beams. Accordingly, the independent support bars 17 (see FIG. 5) may each be longer than the distance separating beams 11, 12 and thus may provide more space for supporting dispensers. Where the support beam 17 is not used to interconnect the vertical beams 11, 12, the independent support beams 17 may be modified to include extensions which provide more horizontal space for suspending bags and the like. For example, the support bar 17 of FIG. 11 comprises a horizontally extending tube 17a which has a slot in its lower surface. A bar 17b having a tab 17c extending therefrom is slideably mounted in tube 17a with the tab 17c extending through the slot. Hooks 18 or the like depend from the tab 17c. If tube 17a is pivotally mounted to beam 11, 12, the support bar 17 may be rotated to any desired position relative to the rack 50. By sliding the bar 17b outwardly with respect to the beam 11, 12, the rack may be used to provide suspension bars 17 extending diametrically from each other or at any other desired position.

Figure 3:
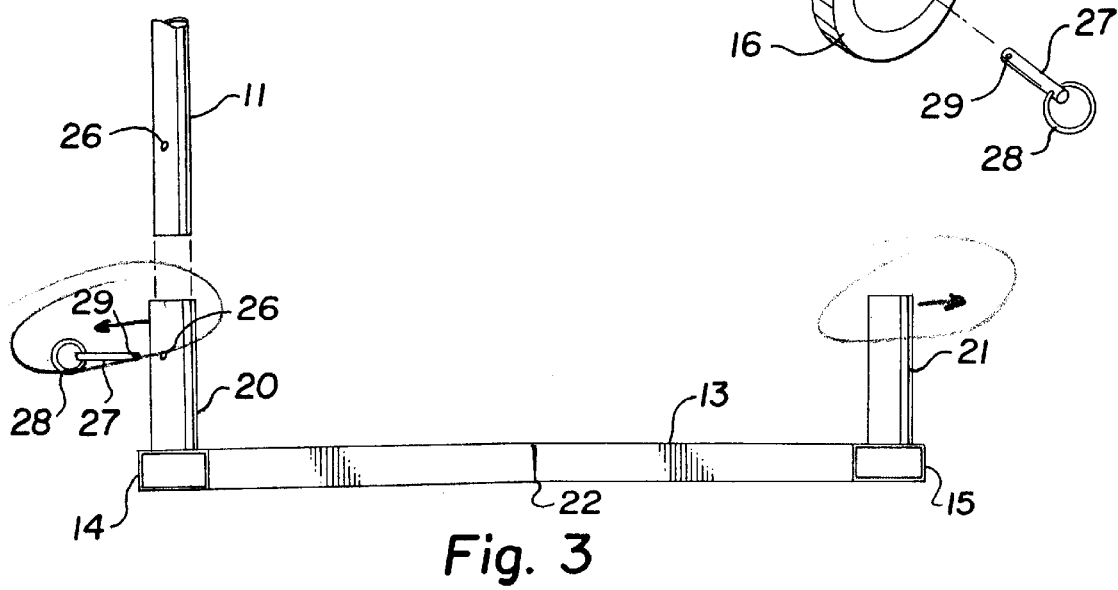
FIG. 3 is a fragmentary view illustrating assembly of the vertical beams on the support base of the mobile dispenser rack of FIG. 1.

In order to securely attach the rack assembly to the base support so as to avoid accidental disassembly an aperture 26 is formed in the overlapping portions of the socket (stud) and vertical beam (see FIG. 3). Aperture 26 preferably passes horizontally through both the socket (stud) and the beam 11, 12 so that a pin, bolt or the like passing through the aperture 26 locks the two parts together and prevents removal of the beam 11, 12 from the socket (stud).

In order to permit rapid and easy assembly and disassembly, the pin is preferably a self-locking pin (referred to herein as a "quick-release pin") which has a resilient key, boss or the like projecting laterally therefrom which may be depressed to permit insertion or removal of the pin from aperture 26. In the preferred embodiment, the quick-release pin carries a gripping ring 28 at one end and a spring-loaded key 29 projecting laterally from the pin near the opposite end. The spring-loaded key 29 is readily depressed by pushing or pulling the pin 27 through apertures 26 but prevents accidental removal of pin 27.

Figure 4:
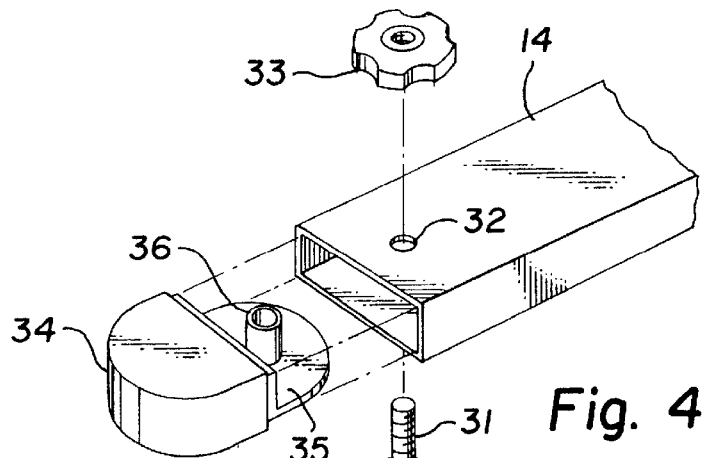
FIG. 4 is an exploded view of one embodiment of wheel attachment assembly of the invention.

Quick-release pin 27 may also be used as the axle which carries wheel 16. As shown in FIG. 4 wheel 16 is supported in a yoke 30 which straddles the wheel 16 and is rotatably attached to a threaded stud 31. In the preferred embodiment, wheel 16 is attached to yoke 30 by a quick-release pin 27 which acts as an axle passing through the yoke 30 and the center of wheel 16. Use of quick-release pin 27 as an axle for the wheels promotes simple, easy and rapid removal of wheels 16 for cleaning or disposal.

In the preferred embodiment yoke 30 is rotatably attached to threaded stud 31 so that the yoke 30 and wheel 16 may swivel when stud 31 is secured to the foot member. As shown in FIG. 4, yoke 30 is attached to foot member 14 by passing threaded stud 31 vertically through a vertical aperture 32 in the foot member and secured with nut 33. In order to permit easy and rapid disassembly and reassembly without the use of tools, nut 33 should be a hand-operable nut such as a wing nut, a large diameter hand-operable nut or other attachment means which may be operated by hand.

Where the foot member 14 is a hollow metal tube structure such as illustrated in FIG. 4, it is preferred that the open end be covered (for purposes of maintaining sterility) and provided with a bumper to protect staff, etc., from the sharp edges of the foot member 14. In the preferred embodiment the cover comprises an end piece 34 which covers or fills the open end of the foot member and a tongue 35 which projects into the hollow foot member. The tongue 35 carries an aperture 36 which is aligned in register with aperture 32 in the foot member so that stud 31 passing through foot member 14 secures the end piece 34 in place. As illustrated in FIG. 4, end piece 34 may be rounded or otherwise shaped to minimize injury or damage to operating personnel or its environment. If desired, end piece 34 may be made from relatively soft material such as plastic, rubber or the like.

The mobile stand of the invention finds particular utility as mobile and self-contained rack for supporting and organizing fluid-dispensing containers. For example, the rack may be used in the operating room by anesthesiologists or other personnel to support and organize a plurality of IV bags on hooks 18. Since the mobile rack of the invention is mounted on quadruplicate wheels, it is structurally stable and will support a large number of IV bags 40 on overhead hooks 18 so that the drip tubes 41 depending therefrom may be arranged in an organized manner for easy use and observation. Furthermore, the embodiment of FIG. 5 permits grouping and arrangement of IV bags and the like on separate support bars 17. Since the bars 17 are rotatable about the vertical beams 11, 12, the IV bags can be segregated into two distinct groups to aid in organization, observation and management of the bags 40 and the drip tubes 41.

Figure 7:
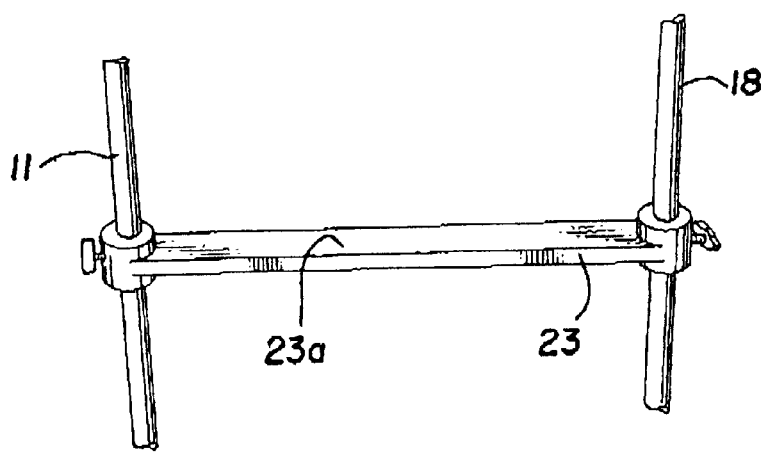
FIG. 7 is a fragmentary view of the parallel vertical beams illustrating an adjustable height bar which employs a flat top surface.

As illustrated in FIGS. 1 and 5, the racks 10, 50 may also support other containers. For example, a gas bottle 42 may be positioned on the base support with cup 43 and/or a clamp 44 carried on one of the vertical beams 11, 12. Similarly, an accessory tray 45 or the like may be adjustably supported as desired on the vertical beams 11, 12. If desired, the moveable crossbar 23 may have a flat surface 23a as shown in FIG. 7 and thus act as a support shelf as well as a crossbar. The crossbar 23 may also be formed to support specific items such as bottles, boxes, etc., and may even support hooks or the like.

Because of the unique stability provided by the H-shaped quadruplicate wheeled base support, the mobile rack of the invention also finds particular utility as a combination walker and cart for ambulatory patients who require liquid injection (such as continuous intravenous injections from IV bags and drip tubes) and/or gas dispensed from pressurized containers or the like. For use as an ambulatory dispenser rack, the patient may grasp the vertical beams 11, 12 or the moveable crossbar 23 and push the rack 10, 50. The rack 10, 50 thus acts as a physical support or stabilizer for the patient while supporting and carrying any required fluid dispensers such as IV bags 40, gas bottles 42, waste collection bags and the like.

Figure 6:
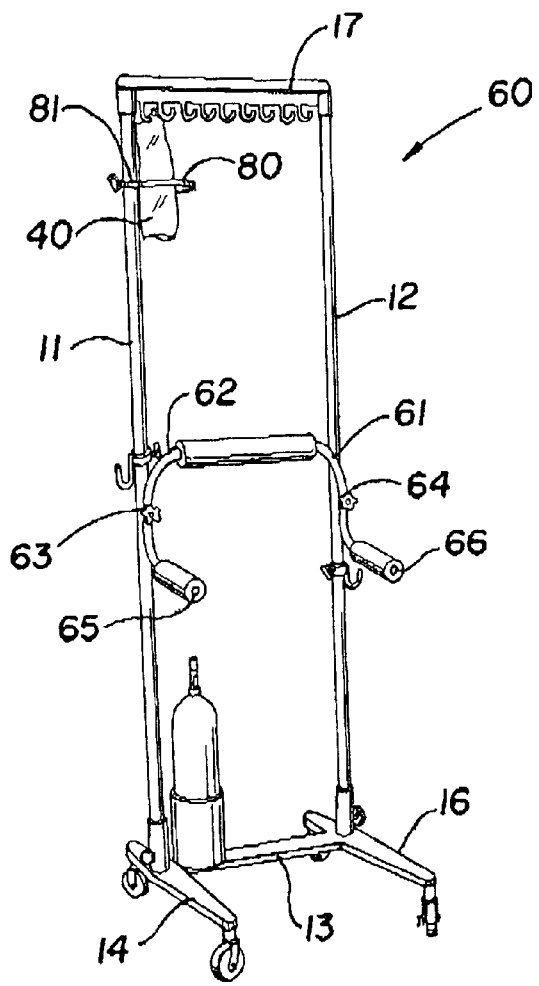
FIG. 6 is a front perspective view of another alternative embodiment of the rack of the invention equipped as a walker to assist ambulatory patients.

In the embodiment 60 shown in FIG. 6 the crossbar 23 has been replaced by a push bar 61. Push bar 61 preferably comprises a single piece of rigid material such as aluminum, steel or the like formed to provide a crossbar 62 interconnecting vertical support portions 63, 64 which are aligned with and joined to vertical beams 11, 12, respectively. In the preferred embodiment vertical portions 63, 64 are attached by passing a stud through a vertical portion 63, 64 and one of a series of vertically arranged holes in a vertical beam 11, 12. The push bar 61 may thus be attached at any desired adjustably selected vertical position on the beams 11, 12. Alternatively, clamps or similar attachments may be used to secure the push bar 61 to the beams 11, 12.

As illustrated in FIG. 6 the ends 65, 66 of the push bar extend rearwardly (substantially horizontally) from the vertical portions 63, 64. The ends 65, 66 thus extend substantially parallel with foot members 14, 16 and may act as handles for pushing the rack 60 while supporting the weight of the patient-operator. Similarly, the horizontally extending crossbar 62 may be used as a push handle and/or a stabilizer support for the operator.

Figure 8:
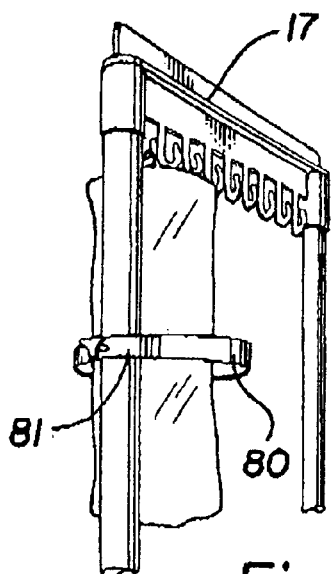
FIG. 8 is a side elevational view of a bag stabilizer deployed on the mobile dispenser rack of the invention.
Figure 9:
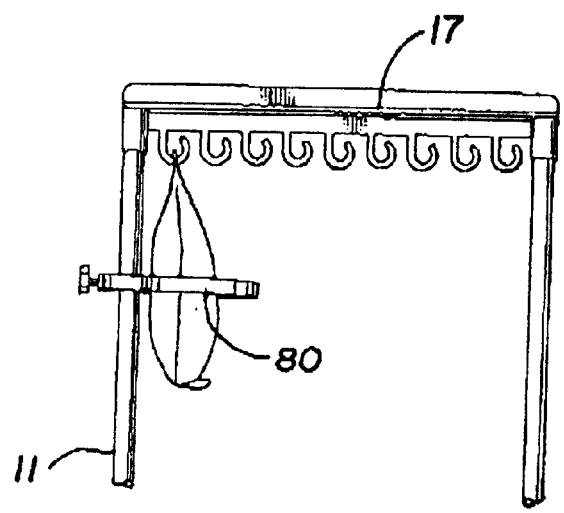
FIG. 9 is a front elevational view of the bag stabilizer of FIG. 8.
Figure 10:
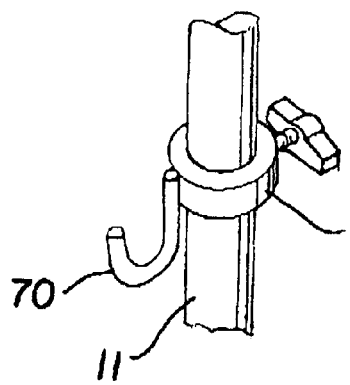
FIG. 10 is a front perspective view of a utility hook deployed on one of the vertical beams of a rack in accordance with the invention.

In the preferred embodiment push bar 61 is a single piece of shaped material which may be readily removed for cleaning or height adjustment. The ends 65, 66 and central portion of crossbar 62 are preferably covered with removeable padding such as sponge rubber or the like which may be replaced as required to maintain sanitation.

Where the rack is used as an ambulatory walker (as, for example, shown in FIG. 6), IV bags or the like suspended from support bar 17 may be subjected to excessive movement. To prevent unnecessary swinging of bags suspended from support bar 17, a stabilizer as shown in FIGS. 8 and 9 may be employed. The stabilizer comprises a stabilizer loop 80 which projects inwardly from one of vertical beams 11, 12 and at least partially surrounds a bag suspended from bar 17. The loop 80 is secured to the beam 11, 12 by an internal clamp 81 or the like which is adjustably moveable along the vertical beams 11, 12. Similarly, a vertically moveable hook 70 may be adjustably supported on beam 11, 12 by clamp 71 or the like to support a waste collection bag or similar utility.

The mobile stand of the invention may be fabricated from any of a variety of conventional materials. For use in sterile environments such as surgical operating rooms and the like, it is preferred that the rack be formed of stainless steel or other suitable materials which may be cleaned and sterilized by conventional means. As disclosed herein, the rack of the invention is uniquely designed to permit rapid, simple and easy disassembly for cleaning and reassembly without using any tools. Each component is suitably sized and shaped for easy sterilization by conventional means. Furthermore, components which are most subject to contamination (such as wheels 16) are removeably mounted so as to permit and encourage easy cleaning or disposal and replacement after each use or as otherwise required.

It will be apparent from the foregoing that the principles of the invention may be used to produce mobile racks for organizing and supporting liquid and/or gas dispensers, collectors and the like. Such racks may be readily and easily disassembled for cleaning to permit repeated use in sterile environments. Such racks are also useful as ambulatory supports for IV dispensers, waste collectors and the like for ambulatory patients. It is to be understood that even though numerous characteristics and advantages of the invention have been set forth in the foregoing description together with details of the structure and function of the invention, this disclosure is to be considered illustrative only. Various changes and modifications may be made in detail, especially in matters of shape, size, arrangement and combination of parts, without departing from the spirit and scope of the invention as defined by the appended claims.

What is claimed:

1. A mobile support rack for dispensing fluids comprising:
    (a) a support base comprising at least one horizontally extending cross member connecting two foot members, each foot member having a central body joined with said cross member and first and second ends extending in opposite directions from and normal to the horizontal axis of said cross member;
    (b) two substantially parallel beams extending substantially vertically from said support base, each of said beams having a first end removeably attached to said support base and a second end suspended substantially vertically above the first end thereof;
    (c) a connecting bar attached to and extending substantially horizontally between said substantially parallel beams; and
    (d) hooks depending from a support bar attached to at least one of said parallel beams at or near the second end of such beam,
        wherein said connecting bar is positioned below the second ends of said parallel beams and said support bar is rotatably mounted in the second end of one of said parallel beams to extend substantially horizontally from such beam and includes hooks depending from the horizontally extending bar.

2. A mobile rack as defined in claim 1 including a second support bar rotatably mounted in the second end of the other of said parallel beams to extend substantially horizontally from such beam.

3. A mobile rack as defined in claim 1 wherein said connecting bar is moveably attached to said substantially parallel bars.

4. A mobile rack as defined in claim 1 wherein said connecting bar has a substantially flat top surface.

5. A mobile support rack for dispensing fluids comprising:
   (a) a support base comprising at least one horizontally extending cross member connecting two foot members, each foot member having a central body joined with said cross member and first and second ends extending in opposite directions from and normal to the horizontal axis of said cross member;
   (b) two substantially parallel beams extending substantially vertically from said support base, each of said beams having a first end removeably attached to said support base and a second end suspended substantially vertically above the first end thereof;
   (c) a connecting bar attached to and extending substantially horizontally between said substantially parallel beams; and
   (d) hooks depending from a support bar attached to at least one of said parallel beams at or near the second end of such beam,
   wherein said cross member is slightly bowed so that the ends thereof are below the central portion thereof.

6. A mobile support rack for dispensing fluids comprising:
   (a) a support base comprising at least one horizontally extending cross member connecting two foot members, each foot member having a central body joined with said cross member and first and second ends extending in opposite directions from and normal to the horizontal axis of said cross member;
   (b) two substantially parallel beams extending substantially vertically from said support base, each of said beams having a first end removeably attached to said support base and a second end suspended substantially vertically above the first end thereof;
   (c) a connecting bar attached to and extending substantially horizontally between said substantially parallel beams; and
   (d) hooks depending from a support bar attached to at least one of said parallel beams at or near the second end of such beam,
   wherein said cross member is bowed by forming at least one notch in the lower surface of said cross member and forcing the sides of the open ends of the notch toward each other.

7. A mobile support rack for dispensing fluids comprising:
   (a) a support base comprising at least one horizontally extending cross member connecting two foot members, each foot member having a central body joined with said cross member and first and second ends extending in opposite directions from and normal to the horizontal axis of said cross member;
   (b) two substantially parallel beams extending substantially vertically from said support base, each of said beams having a first end removeably attached to said support base and a second end suspended substantially vertically above the first end thereof;
   (c) a connecting bar attached to and extending substantially horizontally between said substantially parallel beams; and
   (d) hooks depending from a support bar attached to at least one of said parallel beams at or near the second end of such beam,
   wherein the first end of each of said parallel beams fits within a socket extending upwardly from said support base.

8. A mobile support rack for dispensing fluids comprising:
   (a) a support base comprising at least one horizontally extending cross member connecting two foot members, each foot member having a central body joined with said cross member and first and second ends extending in opposite directions from and normal to the horizontal axis of said cross member;
   (b) two substantially parallel beams extending substantially vertically from said support base, each of said beams having a first end removeably attached to said support base and a second end suspended substantially vertically above the first end thereof;
   (c) a connecting bar attached to and extending substantially horizontally between said substantially parallel beams; and
   (d) hooks depending from a support bar attached to at least one of said parallel beams at or near the second end of such beam,
   wherein the first end of each of said parallel beams is hollow and fits over a stud extending upwardly from said support base.

9. A mobile rack as defined in claim 7 including a quick-release pin extending substantially horizontally through each of said parallel beams and the socket in which the first end of said beam is supported.

10. A mobile rack as defined in claim 8 including a quick-release pin extending substantially horizontally through each of said parallel beams and the stud on which the first end of said beam is supported.

11. A mobile support rack for dispensing fluids comprising:
   (a) a support base comprising at least one horizontally extending cross member connecting two foot members, each foot member having a central body joined with said cross member and first and second ends extending in opposite directions from and normal to the horizontal axis of said cross member;
   (b) two substantially parallel beams extending substantially vertically from said support base, each of said beams having a first end removeably attached to said support base and a second end suspended substantially vertically above the first end thereof;
   (c) a connecting bar attached to and extending substantially horizontally between said substantially parallel beams;
   (d) hooks depending from a support bar attached to at least one of said parallel beams at or near the second end of such beam, and
   (e) clamp means for securing accessories to at least one of said parallel beams.

12. A mobile rack as defined in claim 10 including guide means secured to said cross member for positioning accessories in said support base.

13. A mobile support rack for dispensing fluids comprising:
   (a) a support base comprising at least one horizontally extending cross member connecting two foot members, each foot member having a central body joined with said cross member and first and second ends extending in opposite directions from and normal to the horizontal axis of said cross member;
   (b) two substantially parallel beams extending substantially vertically from said support base, each of said beams having a first end removeably attached to said support base and a second end suspended substantially vertically above the first end thereof;

(c) a connecting bar attached to and extending substantially horizontally between said substantially parallel beams;

(d) hooks depending from a support bar attached to at least one of said parallel beams at or near the second end of such beam, and (e) a stabilizer mounted on one of said parallel beams which at least partially surrounds any bag suspended from said support bar.

14. A mobile support rack for dispensing fluids comprising:

(a) a support base comprising at least one horizontally extending cross member connecting two foot members, each foot member having a central body joined with said cross member and first and second ends extending in opposite directions from and normal to the horizontal axis of said cross member;

(b) two substantially parallel beams extending substantially vertically from said support base, each of said beams having a first end removeably attached to said support base and a second end suspended substantially vertically above the first end thereof;

(c) a connecting bar attached to and extending substantially horizontally between said substantially parallel beams;

(d) hooks depending from a support bar attached to at least one of said parallel beams at or near the second end of such beam, and (e) a wheel attached to each end of each of said foot members.

15. A mobile rack as defined in claim 14 wherein each wheel is supported in a yoke by an axle which passes through the yoke and the center of the wheel and wherein said axle is a quick-release pin.

16. A mobile rack as defined in claim 14 wherein (a) the end of at least one of said foot members has a substantially vertical aperture passing therethrough;

(b) the wheel attached to said end is supported on an axle passing through a yoke and the center of the wheel; and (c) said yoke is supported on a threaded stud which passes vertically through said vertical aperture and is secured to said foot member with a nut which mates with said threaded stud.

17. A mobile rack as defined in claim 16 wherein the end of said foot member is hollow and wherein a cover is mounted in said hollow end to cover the open end of said foot member, said cover comprising an end piece which covers or fills the open end of said foot member and a tongue which extends from said end piece into said foot member with an aperture on said tongue which is in register with the vertical aperture passing through said foot member.

18. A mobile support rack comprising:

(a) a support base comprising at least one horizontally extending cross member connecting two foot members, each foot member having a central body joined with said cross member and first and second ends extending in opposite directions from and normal to the horizontal axis of said cross member;

(b) two substantially parallel beams extending substantially vertically from said support base, each of said beams having a first end removeably attached to said support base and a second end suspended substantially vertically above the first end thereof;

(c) a connecting bar attached to and extending substantially horizontally between said substantially parallel beams; and (d) means secured to at least one of said parallel beams for supporting a fluid container,
wherein said connecting bar comprises a single bar shaped to provide a substantially horizontal bar suspended between said parallel beams; two vertical portions, one of each of which is secured to one of said parallel beams; and an end portion extending substantially horizontally from each of said vertical portions and substantially parallel with said foot members.

19. A mobile support rack comprising:

(a) a support base comprising at least one horizontally extending cross member connecting two foot members, each toot member having a central body joined with said cross member and first and second ends extending in opposite directions from and normal to the horizontal axis of said cross member;

(b) two substantially parallel beams extending substantially vertically from said support base, each of said beams having a first end removeably attached to said support base and a second end suspended substantially vertically above the first end thereof;

(c) a connecting bar attached to and extending substantially horizontally between said substantially parallel beams;

(d) means secured to at least one of said parallel beams for supporting a fluid container, and (e) padding removeably secured to said connecting bar.

20. A mobile rack as defined in claim 18 including padding removeably secured to said end portions.

* * * * *

UNITED STATES PATENT AND TRADEMARK OFFICE
CERTIFICATE OF CORRECTION

PATENT NO.     : 6,390,311 B1
DATED          : May 21, 2002
INVENTOR(S)    : Paul Belokin It is certified that error appears in the above-identified patent and that said Letters Patent is hereby corrected as shown below:

Column 1,
Line 45, "beam. s" should read -- beams --

Column 10,
Line 34, "toot" should read -- foot --

Signed and Sealed this

Twenty-third Day of July, 2002

Attest:

Attesting Officer

JAMES E. ROGAN
Director of the United States Patent and Trademark Office